US010052453B2

(12) United States Patent
Racz

(10) Patent No.: US 10,052,453 B2
(45) Date of Patent: Aug. 21, 2018

(54) RETROFITTED NEURAL INJECTION SYSTEM AND RELATED METHODS

(71) Applicant: Custom Medical Applications, Farmers Branch, TX (US)

(72) Inventor: Nicholas Sandor Racz, Coppell, TX (US)

(73) Assignee: Custom Medical Applications, Farmers Branch, TX (US)

( * ) Notice: Subject to any disclaimer, the term of this patent is extended or adjusted under 35 U.S.C. 154(b) by 463 days.

(21) Appl. No.: 14/188,110

(22) Filed: Feb. 24, 2014

(65) Prior Publication Data

US 2014/0165357 A1    Jun. 19, 2014

Related U.S. Application Data

(62) Division of application No. 12/139,223, filed on Jun. 13, 2008, now Pat. No. 8,690,832.

(60) Provisional application No. 60/943,824, filed on Jun. 13, 2007.

(51) Int. Cl.
*A61M 25/00* (2006.01)
*A61M 5/32* (2006.01)
*A61B 17/34* (2006.01)

(52) U.S. Cl.
CPC ...... *A61M 25/0009* (2013.01); *A61M 5/3291* (2013.01); *A61B 17/3401* (2013.01); *Y10T 29/49716* (2015.01)

(58) Field of Classification Search
CPC .......... B29C 45/14; B29C 2045/14286; B29C 2045/14295; B29C 45/14598; B29C 2045/14606; B29C 45/14622; B29C 70/68; A61B 2017/3419; A61B 17/3401; A61B 17/34; A61M 5/3291
USPC .... 604/272, 264, 506, 500, 162, 171, 164.1; 264/259, 512
See application file for complete search history.

(56) References Cited

U.S. PATENT DOCUMENTS

| 2,899,959 | A | * | 8/1959 | Ginsburg | ...................... 604/174 |
| 2,922,420 | A |   | 1/1960 | Cheng |  |
| 3,469,572 | A | * | 9/1969 | Nehring | .......................... 604/66 |

(Continued)

OTHER PUBLICATIONS http://www.oxforddictionaries.com/us/definition/american_english/ethylene, Oxford University Press 2015.*

(Continued)

*Primary Examiner* — Manuel Mendez
(74) *Attorney, Agent, or Firm* — TraskBritt

(57) ABSTRACT

Various embodiments may include methods of manufacture of a retrofitted neural injection system. Various embodiments may include acquiring an injection needle comprising a hollow cannula with an open distal end. Then, forming at least one side port in the hollow cannula proximate to the distal end. Then, sealing the open distal end of the hollow cannula with a biocompatible sealant so as to eliminate fluid communication between an inside and an outside of the hollow cannula via the distal end. In some embodiments, the biocompatible sealant may be comprised of a thermosetting material. In some embodiments, the biocompatible sealant may be comprised of a cured epoxy resin. In some embodiments, the biocompatible sealant may be comprised of an aliphatic polymer. In some embodiments, the biocompatible sealant may be comprised of a polyfluorocarbon.

20 Claims, 3 Drawing Sheets

(56) References Cited

U.S. PATENT DOCUMENTS

| | | | |
|---|---|---|---|
| 3,565,074 A | | 2/1971 | Foti |
| 3,726,269 A | * | 4/1973 | Webster, Jr. ............ A61B 5/028 600/526 |
| 3,817,248 A | * | 6/1974 | Buckles .................... A61F 6/14 128/DIG. 12 |
| 3,856,009 A | | 12/1974 | Winnie |
| 3,995,619 A | * | 12/1976 | Glatzer ............... A61B 10/0275 600/550 |
| 4,094,195 A | * | 6/1978 | Friswell et al. ............ 73/864.21 |
| 4,230,123 A | | 10/1980 | Hawkins, Jr. |
| 4,240,433 A | * | 12/1980 | Bordow ............. A61B 17/3496 604/162 |
| 4,308,875 A | | 1/1982 | Young |
| 4,317,445 A | | 3/1982 | Robinson |
| 4,629,450 A | | 12/1986 | Suzuki |
| 4,781,692 A | | 11/1988 | Jagger |
| 4,909,793 A | | 3/1990 | Vining |
| 4,924,881 A | | 5/1990 | Brewer |
| 4,967,766 A | | 11/1990 | Bradshaw |
| 4,973,313 A | | 11/1990 | Katsaros |
| 4,994,034 A | | 2/1991 | Botich |
| 5,106,376 A | | 4/1992 | Mononen |
| 5,129,404 A | | 7/1992 | Spehr |
| 5,228,455 A | | 7/1993 | Barcel |
| 5,242,410 A | | 9/1993 | Melker |
| 5,250,035 A | | 10/1993 | Smith |
| 5,290,267 A | | 3/1994 | Zimmermann |
| 5,304,141 A | | 4/1994 | Johnson |
| 5,312,360 A | | 5/1994 | Behl |
| 5,336,191 A | | 8/1994 | Davis |
| 5,336,198 A | * | 8/1994 | Silver et al. .................. 604/195 |
| 5,344,439 A | | 9/1994 | Otten |
| 5,397,512 A | * | 3/1995 | Sloane, Jr. ........ A61M 25/0009 219/121.64 |
| 5,449,351 A | * | 9/1995 | Zohmann .............. A61M 25/06 604/158 |
| 5,480,389 A | | 1/1996 | McWha |
| 5,531,692 A | * | 7/1996 | Rogers ................ A61M 5/3287 604/110 |
| 5,571,091 A | | 11/1996 | Davis |
| 5,573,519 A | | 11/1996 | Zohmann |
| 5,628,734 A | | 5/1997 | Hatfalvi |
| 5,637,399 A | * | 6/1997 | Yoshikawa et al. .......... 428/369 |
| 5,669,882 A | | 9/1997 | Pyles |
| 5,730,749 A | | 3/1998 | Battenfield |
| 5,800,407 A | | 9/1998 | Eldor |
| 5,800,445 A | | 9/1998 | Ratcliff |
| 5,817,074 A | | 10/1998 | Racz |
| 5,836,914 A | | 11/1998 | Houghton |
| 5,865,806 A | | 2/1999 | Howell |
| 5,871,470 A | | 2/1999 | McWha |
| 5,954,694 A | * | 9/1999 | Sunseri ............. A61M 25/0009 604/103 |
| 6,345,044 B1 | | 2/2002 | Edgar, III |
| 6,371,943 B1 | * | 4/2002 | Racz et al. .................... 604/274 |
| 6,383,145 B1 | | 5/2002 | Worm |
| 6,387,163 B1 | | 5/2002 | Leong |
| 6,517,521 B1 | * | 2/2003 | Ly ........................ A61M 5/329 604/239 |
| 6,547,769 B2 | | 4/2003 | VanTassel ........... A61M 5/3286 604/264 |
| 6,551,253 B2 | | 4/2003 | Worm |
| 6,558,353 B2 | | 5/2003 | Zohmann |
| 6,584,335 B1 | * | 6/2003 | Haar .................. A61B 5/14532 600/322 |
| 6,855,132 B2 | | 2/2005 | VanTassel |
| 6,949,087 B2 | | 9/2005 | VanTassel |
| 6,968,238 B1 | | 11/2005 | Kuzma |
| 7,937,981 B2 | * | 5/2011 | Reynolds ......... A61B 17/06066 163/5 |
| 2001/0049499 A1 | * | 12/2001 | Lui ...................... A61M 39/06 604/164.05 |
| 2002/0138042 A1 | * | 9/2002 | Llorach ................ A61M 5/343 604/187 |
| 2003/0055379 A1 | | 3/2003 | Rosiello |
| 2003/0233101 A1 | | 12/2003 | Lubock et al. |
| 2004/0002729 A1 | * | 1/2004 | Zamore ................ A61L 31/048 606/194 |

OTHER PUBLICATIONS

James Heavner et al., Sharp Versus Blunt Needle: A Comparative Study of Penetration of Internal Structures and Bleeding in Dogs, Pain Practice, Sep. 2003, 226-231, 3-3.

Final Office Action from United States Patent and Trademark Office dated Oct. 29, 2010, in U.S. Appl. No. 11/853,785.

Non-Final Office Action from United States Patent and Trademark Office dated Jul. 15, 2010, in U.S. Appl. No. 11/853,785.

Final Office Action from United States Patent and Trademark Office dated Mar. 9, 2010, in U.S. Appl. No. 11/853,785.

Non-Final Office Action from United States Patent and Trademark Office dated Sep. 29, 2009, in U.S. Appl. No. 11/853,785.

Final Office Action from United States Patent and Trademark Office dated Jun. 15, 2009, in U.S. Appl. No. 11/853,785.

Non-Final Office Action from United States Patent and Trademark Office dated Nov. 7, 2008, in U.S. Appl. No. 11/853,785.

Final Office Action from United States Patent and Trademark Office dated Mar. 22, 2010, in U.S. Appl. No. 12/139,233.

Non-Final Office Action from United States Patent and Trademark Office dated Jun. 8, 2009, in U.S. Appl. No. 12/139,233.

Final Office Action from United States Patent and Trademark Office dated May 27, 2010, in U.S. Appl. No. 11/853,671.

Non-Final Office Action from United States Patent and Trademark Office dated Nov. 12, 2009, in U.S. Appl. No. 11/853,671.

Final Office Action from United States Patent and Trademark Office dated Jul. 22, 2009, in U.S. Appl. No. 11/853,671.

Non-Final Office Action from United States Patent and Trademark Office dated Mar. 6, 2009, in U.S. Appl. No. 11/853,671.

Final Office Action from United States Patent and Trademark Office dated Feb. 2, 2012, in U.S. Appl. No. 11/853,785.

Final Office Action from United States Patent and Trademark Office dated Sep. 5, 2013, in U.S. Appl. No. 11/853,785.

Non-Final Office Action from United States Patent and Trademark Office dated Oct. 28, 2011, in U.S. Appl. No. 11/853,785.

Non-Final Office Action from United States Patent and Trademark Office dated Aug. 15, 2012, in U.S. Appl. No. 11/853,785.

Non-Final Office Action from United States Patent and Trademark Office dated Feb. 7, 2013, in U.S. Appl. No. 11/853,785.

Huntoon, Marc A., Anatomy of the certivical intervertebral foramina: vulnerable arteries and ischemic neurologic injuries after transforaminal epidural injections, Pain, 2005, pp. 104-111, vol. 117, Elsevier B.V.

Lirk, Phillipp et al., Cervical and High Thoracic Ligamentum Flavum Frequently Fails to Fuse in the Midline, Anesthesiology, Dec. 2003, pp. 1387-1390, vol. 99, No. 6, Lippincott Williams & Wilkins, Inc.

Racz, Gabor B et al., Cervical Spinal Canal Loculation and Secondary Ischemic Cord Injury—PVCS—Perivenous Counter Spred—Danger Sign!, Pain Practice, 2008, pp. 399-403, vol. 8, No. 5.

Scanlon, Graham C. et al., Cervical Transforaminal Epidural Steroid Injections, Spine, 2007, pp. 1249-1256, vol. 32, No. 11, Lippincott Williams & Wilkins, Inc.

Houten, John K. et al., Paraplegia after lumbosacral nerve root block: report of three cases, The Spine Journal 2, 2002, pp. 70-75, Elsevier.

Glaser, Scott E et al., Root Cause Analysis of Paraplegia Following Transforaminal Epidural Steroid Injections: The 'Unsafe' Triangle, Pain Physician Journal, May/Jun. 2010, pp. 237-244, vol. 13, ISSN: 1533-3159.

Akins, E. William et al., The Blunt Needle: A New Percutaneous Access Device, AJR, Jan. 1989, pp. 181-182, vol. 152, American Roentgen Ray Society.

Non-Final Office Action from United States Patent and Trademark Office dated Dec. 14, 2017, in U.S. Appl. No. 14/187,983.

(56) References Cited

OTHER PUBLICATIONS

Final Office Action from United States Patent and Trademark Office dated Mar. 15, 2018, in U.S. Appl. No. 14/187,983.

* cited by examiner

RETROFITTED NEURAL INJECTION SYSTEM AND RELATED METHODS

CROSS-REFERENCE TO RELATED APPLICATIONS

This application is a divisional of U.S. patent application Ser. No. 12/139,233, filed Jun. 13, 2008, now U.S. Pat. No. 8,690,832, issued Apr. 8, 2014, which claims priority to U.S. Provisional Patent Application Ser. No. 60/943,824, filed Jun. 13, 2007. This application is also related to U.S. patent application Ser. No. 14/187,983, filed Feb. 24, 2014, pending.

FIELD OF INVENTION

The present invention generally relates to injection systems and related methods of manufacture and use.

BACKGROUND OF THE INVENTION

Needles and needle systems are used extensively in a wide variety of procedures that are performed in various fields of medicine, such as cardiology, radiology, urology, interventional pain management, and internal medicine. The use of needles and needle systems in invasive procedures in various medical fields has become routine due, in part, to the ability of needles to pass through most tissues without causing significant destruction to the tissues. Conventional needles have an orifice or a port at the distal tip of the needle. Distal tips of needles are more liable to clog as the tip of the needle is used for penetration of tissue to access the site of treatment. Additionally, there exists a greater chance of leakage of the agent being delivered, using conventional needles. Needles with orifices located along the length of the needle are routinely used for aspiration purposes as well as for delivering anesthesia. Specifically, a variety of needles having side ports are used for delivery of spinal anesthesia. This configuration reduces the chance of the inability to deliver anesthesia due to clogging of the opening at the needle tip.

A very successful embodiment of a needle with an opening at the distal end portion and with a side port is disclosed in U.S. Pat. No. 5,817,074 ("the '074 patent"). The '074 patent discloses a stellate ganglion sympathetic block needle having a side port positioned at a predetermined distance from the opening of the distal tip. The stellate ganglion sympathetic block needle allows for an effective stellate ganglion sympathetic block even if the needle is placed such that the needle distal opening is under the anterior longitudinal ligament, which results in the needle distal opening being constricted, thereby interfering with the injection of the anesthesia. When this interference occurs, the side port of the stellate ganglion sympathetic block needle allows directional injection onto the surface of the anterior longitudinal ligament in order to spread onto the surface of the longus coli muscle toward the stellate ganglion, thereby achieving an effective stellate ganglion sympathetic block. This invention has found wide applicability; however, certain procedures might prefer a needle with a blocked distal tip and only side port(s) for the administration of therapeutic, diagnostic or prophylactic agents while retaining the sharp point of the distal tip to maneuver and penetrate certain tissues to access treatment sites.

Needles with a blocked tip (distal end) and an open side portal are used for procedures such as thoracentesis, which involves inserting the needle through the thoracic cage into the pleural space between the lung and the chest wall to draw off fluid for diagnostic or therapeutic purposes. Thoracentesis needles generally consist of an orifice free, sharp conical end and a circular side hole for draining fluid. However, these needles are pre-made with an enclosed end, making them much more expensive than traditional open-ended beveled needles to manufacture.

Accordingly, it would be desirable to create a neural injection system that is primarily composed of a traditional open-ended needle system, which is common and inexpensive, and retrofit such a needle to provide a sharp-tipped, open side port, closed distal end, neural injection system.

SUMMARY OF THE INVENTION

The summary of the invention is not intended to represent each embodiment or every aspect of the present invention.

Various embodiments may include a retrofitted neural injection system comprising: an at least partially hollow cannula with a sharp distal end, wherein the distal end has a port, and the partially hollow cannula is defined by a first inside diameter, a first outside diameter, a first length, and at least one side port in fluid communication between the inside and the outside of the hollow cannula, located coaxially at a predetermined distance from the distal end, wherein the port at the distal end is sealed to eliminate fluid communication between the inside and the outside of the hollow cannula via the distal end.

Further, various embodiments may include a method of treatment for an individual in need thereof comprising locating a site for treatment in the individual; adjusting the retrofitted neural injection system described above; such that the system is positioned relative to the individual at a desired insertion point and orientation; inserting at the site at least a portion of the retrofitted neural injection system described above; maneuvering the distal end of the retrofitted neural injection system inside the individual proximate to the site; and treating the individual.

Another embodiment may include a method of retrofitting a needle comprising acquiring an injection needle comprising a hollow cannula with an open distal end; forming at least one side port in the hollow cannula proximate to the distal end so as to permit fluid communication between the inside and the outside of the hollow cannula via the side port; and sealing the open distal end of the hollow cannula with a sealant so as to eliminate fluid communication between the inside and the outside of the hollow cannula via the distal end.

Various embodiments may also include a system for delivering an agent in vivo in an individual in need thereof comprising: means for locating a site for delivery in the individual; means for adjusting the retrofitted neural injection system described above; such that the system is positioned relative to the individual at a desired insertion point and orientation; means for inserting at the site at least a portion of the retrofitted neural injection system of claim 1; means for maneuvering the distal end of the retrofitted neural injection system inside the individual proximate to the site; and means for delivering the agent.

Yet another embodiment may be a kit comprising the retrofitted neural injection system described above; and at least one agent, where the agent may be a therapeutic agent, a diagnostic agent or a prophylactic agent.

The foregoing has outlined rather broadly the features and technical advantages of the present invention in order that the detailed description of the invention that follows may be better understood. Additional features and advantages of the invention will be described hereinafter, which form the subject of the claims of the invention.

BRIEF DESCRIPTION OF THE FIGURES

The foregoing summary, as well as the detailed description of the preferred embodiment of the invention, will be better understood when read in conjunction with the accompanying drawings. It should be understood, however, that the invention is not limited to the precise arrangements and instrumentalities shown herein. The components in the drawings are not necessarily to scale, emphasis instead being placed upon clearly illustrating the principles of the present invention. Moreover, in the drawings, like reference numerals designate corresponding parts throughout the several views.

The invention may take physical form in certain parts and arrangement of parts. For a more complete understanding of the present invention, and the advantages thereof, reference is now made to the following descriptions taken in conjunction with the accompanying drawings, in which.

DETAILED DESCRIPTION OF THE INVENTION

Figure 1:
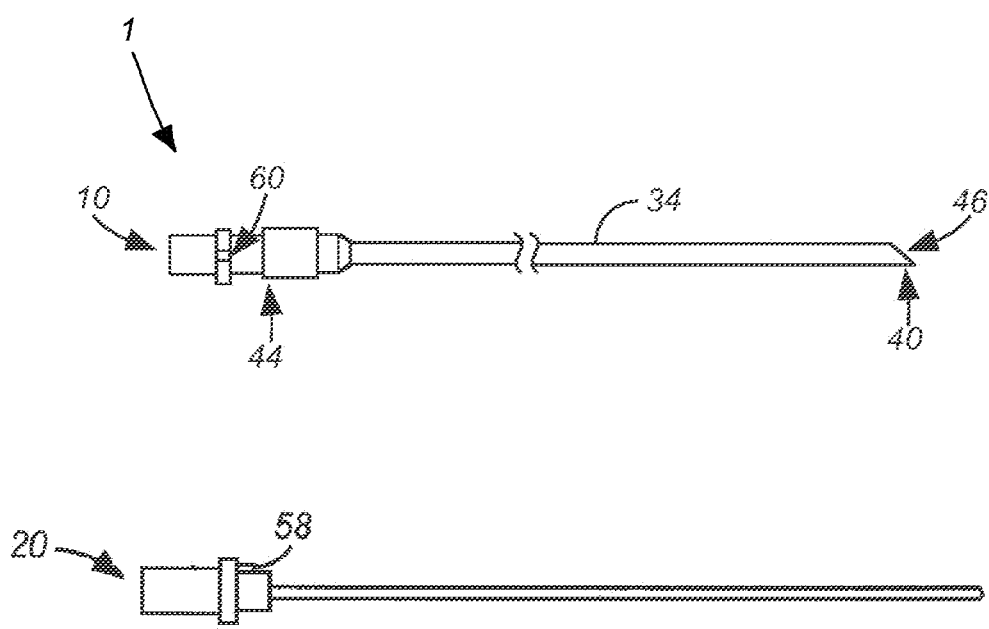
FIG. 1 is an illustration of a traditional injection system found in the prior art.
Figure 2:
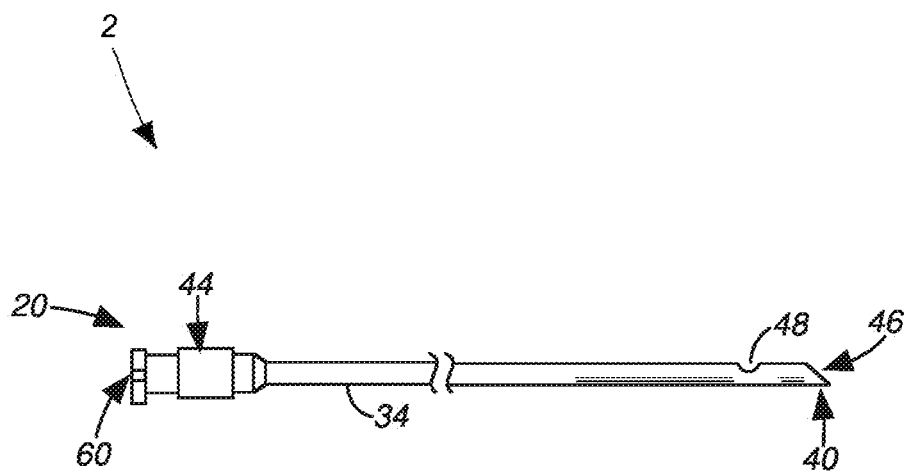
FIG. 2 is an illustration of an embodiment of a retrofitted neural injection system.
Figure 3:
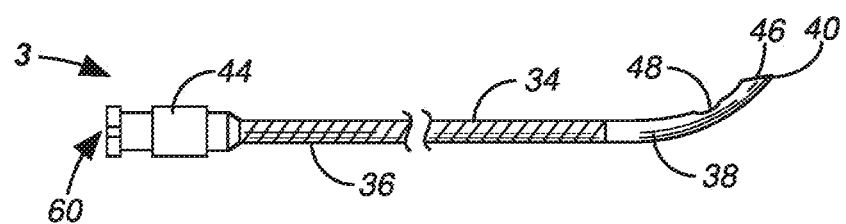
FIG. 3 is an illustration of an embodiment of a retrofitted neural injection system with a rigid bend in the cannula.

The principles of the present invention and their advantages are best understood by referring to FIGS. 1-3 of the drawings, like numerals being used for like and corresponding parts of the various drawings.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

In the following descriptions and examples, specific details are set forth such as specific quantities, sizes, etc., to provide a thorough understanding of the present invention. However, it will be obvious to those skilled in the art that the present invention may be practiced without such specific details. In many cases, details concerning such considerations and the like have been omitted inasmuch as such details are not necessary to obtain a complete understanding of the present invention and are within the skills of persons of ordinary skill in the relevant art. It is therefore contemplated that the claims will cover any such modifications or embodiments that fall within the true scope of the invention.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition.

The term "attached," or any conjugation thereof describes and refers the at least partial connection of two items.

Exemplary, non-limiting embodiments of medical instrument, neural injection systems, and the like that can be modified according to various teachings include, but are not limited to, U.S. Pat. No. 6,949,087; U.S. Pat. No. 6,855,132; U.S. Pat. No. 6,558,353; U.S. Pat. No. 6,547,769; U.S. Pat. No. 6,387,163; U.S. Pat. No. 6,245,044; U.S. Pat. No. 5,871,470; U.S. Pat. No. 5,865,806; U.S. Pat. No. 5,836,914; U.S. Pat. No. 5,817,074; U.S. Pat. No. 5,800,445; U.S. Pat. No. 5,730,749; U.S. Pat. No. 5,669,882; U.S. Pat. No. 5,628,734; U.S. Pat. No. 5,573,519; U.S. Pat. No. 5,571,091; U.S. Pat. No. 5,480,389; U.S. Pat. No. 5,466,225; U.S. Pat. No. 5,336,191; U.S. Pat. No. 5,312,360; U.S. Pat. No. 5,304,141; U.S. Pat. No. 5,250,035; U.S. Pat. No. 5,242,410; U.S. Pat. No. 5,106,376; U.S. Pat. No. 4,994,034; U.S. Pat. No. 4,973,313; U.S. Pat. No. 4,629,450; U.S. Pat. No. 4,317,445; U.S. Pat. No. 4,308,875; U.S. Pat. No. 4,230,123; U.S. Pat. No. 3,856,009; U.S. Pat. No. 3,565,074; and U.S. Pat. No. 2,922,420, the contents of which are hereby incorporated by reference as if they were presented herein in their entirety. In general, any catheter may be used with the various embodiments of the present invention.

A "fluid" is a continuous, amorphous substance whose molecules move freely past one another and that has the tendency to assume the shape of its container, for example, a liquid or a gas.

Any agent that can be injected through a needle can be delivered using the inventive method. Typical agents might include drugs, small molecules, pharmaceutical agents, diagnostic agents, biological molecules, proteins, peptides, antibodies, polynucleotides, RNA, DNA, viruses, cells, and combinations thereof. Agents may range in size from small organic molecules to macromolecules such as DNA to intact cells. The agent to be delivered to the injection site may be therapeutic (e.g., chemotherapeutic drug, antibiotic), prophylactic (e.g., vaccine), or diagnostic (e.g., contrast agent for magnetic resonance imaging, labeled metabolite).

Drugs include any compound useful in the treatment or prevention of a disease. In a particularly preferred embodiment, the drug is an antibiotic, anti-viral agent, anesthetic, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, p-adrenergic blocking agent, diuretic, cardiovascular active agent, vasoactive agent, non-steroidal anti-inflammatory agent, nutritional agent, etc. A combination of drugs may be used in the present invention. The drug may also be delivered in various forms, for example, the drug may be encapsulated, or the drug may be in a time release form.

Therapeutic prophylactic or diagnostic agents to be delivered may also include biological molecules such as proteins, peptides, polynucleotides, and oligonucleotides. Examples of proteins or peptides include insulin, cytokines, growth factors, erythropoietin, antibodies, antibody fragments, etc. Polynucleotides may be delivered for gene therapy and anti-sense therapy.

In addition to drugs, small molecules, and biological molecules, the invention may be used to deliver viruses and cells. Particularly preferred viruses and cells are those that are therapeutic. Viruses with altered genomes may be used in gene therapy as vectors to introduce a foreign gene into the patient's cells.

Further, agents used for delivery with the inventive method disclosed herein may also include cells. Any type of cell or mixture of cells may be transplanted using the inventive method.

The term "medicament(s)" means and refers to all types of fluidic substances that have a beneficial, desired or therapeutic effect. Non-limiting examples of medicaments suitable for use in the invention methods include anesthesia, biologically active agents, such as small molecule drugs, proteinaceous substances, polynucleotides or nucleic acids (e.g., heterologous DNA, or RNA) and vectors, liposomes, and the like, containing such nucleic acids or polynucleotides, as well as liquid preparations or formulations thereof.

The term "medical instrument" means and refers to any item, instrument or structure capable of connecting to a catheter, such as, but not limited to, a stimulation device, tubing, piping, a medicament delivery system, a meter, a liquid repository (e.g., an IV bag), a syringe, or the like.

The term "normal insertion procedure" means and refers to a typical surgical or insertion procedure as disclosed in Heavner et al., "Sharp Versus Blunt Needle: A Comparative Study of Penetration of Internal Structures and Bleeding in Dogs," 2003, World Institute of Pain, Pain Practice, 3:3, 226-231.

The term "stylet" means and refers to a small poniard. Stylets of the preset invention are capable of being hollow, but such is not required.

Other than in the operating examples, or where otherwise indicated, all numbers expressing quantities of ingredients or reaction conditions used herein are to be understood as modified in all instances by the term "about."

Various embodiments include a retrofitted neural injection system and related methods of manufacture and use with at least one benefit of enhanced injection characteristics, increased operational efficiency, reduced cost per unit, reduced incidence of injury through intraneural or intravascular injection, reduced incidence of injury through pricking or piercing, or the like.

Various embodiments include a retrofitted neural injection system, which includes an at least partially hollow cannula. The cannula is defined by a first inside diameter, a first outside diameter, a first length, a side port located coaxially along the cannula for fluid communication between the inside and the outside of the hollow cannula, and a sealed distal end. In some embodiments, the system also includes a stylet, wherein the stylet is capable of being releasably locked in a first position within the hollow cannula and extends up to a first length of the hollow cannula. In some embodiments, the hollow cannula proximate to the distal end includes a rigid bend so as to facilitate placement of the distal end adjacent to a target site.

Various embodiments also include methods and devices that are designed for injection of minute amounts of fluid medicaments into tissue or a body wall, for example, an interior body wall. The therapeutic amount of the medicament to be administered according to a method of the invention may vary depending upon the therapeutic goal to be accomplished, the size and age of the subject, the pharmacokinetics of the injectate, and the like.

Various embodiments are designed for treatment of a target tissue(s) at a target site. In an embodiment, treatment of a tissue may be at least one of probing, ablation, stimulating, or the like. In general, treatments capable with various embodiments can be any treatment common in the art and should not be limited by the present disclosure.

A cannula associated with various embodiments may be a cylindrical structure extending from a proximal end to a distal end. The length from the proximal end to the distal end, traveling along the length of the cannula is known as the first length. In various embodiments where a bend in the cannula exists, the first length may be longer than the linear distance from the proximal end to the distal end. In an embodiment, the cannula is of a generally constant circumference. The cannula is capable of being differentiated by an inside diameter and an outside diameter. In an embodiment, an outside diameter is between about 0.0355 to about 0.03600 mm and an inside diameter is between about 0.0230 to about 0.0245 mm. In an alternative embodiment, an outside diameter between about 0.0205 to 0.280 mm and an inside diameter between about 0.0155 to 0.0170 mm. In various embodiments, an inside diameter and an outside diameter are capable of being any desired length and any particular length should not be construed as a limitation on the scope of the appended claims.

In various embodiments, a distal end of the at least partially hollow cannula may take various shapes. In an embodiment, the distal tip may have the traditional beveled angular plane shape. In another embodiment, the distal tip is squared with the perpendicular of the lengthwise plane of the cannula. In another embodiment, the distal tip forms a partial bevel, wherein the leading portion of the shaped tip is of a traditional bevel form and the remainder of the tip is formed in a non-beveled shape, such as a stair step. Regardless of the shape of the distal end of the cannula, the distal end of the cannula should be capable of being sealed by a material so as to close the original open distal end of the cannula.

In various embodiments, a sealant is applied to provide a hermetic seal at the distal end of the at least partially hollow cannula. The seal may be used to block all fluid flow through the formerly open distal end of the cannula. In various embodiments, the sealant may be applied in a moderate amount so that the cutting and leading action of the distal tip is not encumbered by a buildup of sealant on the distal tip. In various embodiments, the sealant may be applied in a moderate amount so that the side port is not encumbered or blocked. In some embodiments, the sealant is composed of a biocompatible material, such as a thermosetting polymer like an epoxy resin. Aliphatic polymers such as polyethylene or polypropylene may be applied in a liquid form and cooled to a solid state on the distal end of the hollow cannula or in monomer form and cured on the surface of the hollow cannula so as to provide a thin, yet resistant film across the open end of the distal end. Another sealant that may be used would be one comprised of a polyfluorocarbon to increase the "slipperiness" of the leading surface. Other sealant materials that may be used are known to those familiar in the medical arts.

In various embodiments, a connector may be about the proximal end of the cannula. A connector may be used as an attachment means for attaching the cannula and an optional further medical instrument. The connection(s) at the proximal end may be any type of connection common in the art, such as, for example, and not by way of limitation, a luer lock connector, a threaded attachment, an interference fit attachment, a clamp, a system utilizing a dowel, two or more of the aforesaid in combination, or the like.

A stylet of various embodiments may extend through at least a portion of the hollow portion of the cannula. In some embodiments, a stylet may be characterized by an outside diameter and a length extending from a proximal end to the distal end, representing the first length. The outside diameter, in various embodiments, is smaller than the first inside diameter of the cannula. In some embodiments, the stylet comprises a side port and is at least partially hollow. In an embodiment, the stylet and the cannula define a passageway for passage of at least one medicament.

In various embodiments, the material of construction may permit the stylet so as to bend within the hollow cannula to conform generally to its internal shape. In some embodiments, the material of construction of the flexible stylet may be of a polymer material. In some embodiments, the material will be made of a biocompatible material. Examples of such embodiments include materials such as polyethylene, polypropylene, and polyfluorocarbons. In some alternative embodiments, the material of construction may be of a metallic material. Examples of embodiments include steel alloys, titanium alloys, and aluminum. In various embodiments, the stylet exhibits elastic deformation in regards to insertion and removal from the cannula.

In various embodiments, the stylet may be capable of being inserted into the cannula so that the distal tip of the stylet may be positioned within the cannula at any point. In an embodiment, the distal end of the stylet may be positioned so that the distal end of the stylet is equivalent with the distal end of the cannula in relation to the proximate end of the cannula. In an alternative embodiment, the distal end of the stylet may extend past the distal end of the cannula. In an alternative embodiment, the distal end of the cannula may extend past the distal end of the stylet.

Various embodiments may fixedly connect, releasably connect, or leave unconnected the flexible stylet and the cannula. In another embodiment, the stylet is capable of sliding within the cannula. In another embodiment, the stylet is releasably secured within the cannula by a locking mechanism, such as, but not limited to, a luer lock, an interference fit, a snap, screw threads, or the like. In an embodiment of a luer lock system, internal male luer threads are located in or about the stylet adjacent to receive and engage a cannula having female luer threads thereon. In other embodiments, the luer lock is reversed. In another embodiment, the stylet is welded to or otherwise fixedly connected to the cannula.

A side port in various embodiments may be a port extending from the exterior of the hollow cannula to the interior of the hollow cannula or the flexible stylet. The shape of the side port may vary. In an embodiment, a port may be circular. In another embodiment, a port may be ovular. In yet another embodiment, a port may be a quadrangular port, such as a rectangle or a square. In still another embodiment, the port is triangular. It can be seen by one skilled in the art that the shape of the port may be formed in any shape sufficient to permit fluid aspiration.

A side port in various embodiments may be further characterized by the associated edge of the port on the cannula or stylet. In an embodiment, a port may have a slightly inwardly beveled edge extending from the exterior surface of the hollow cannula to the interior surface. In an alternative embodiment, a port may have a slightly outwardly beveled edge extending from the interior surface of the hollow cannula to the exterior surface. In an embodiment, the degree of bevel may be used to change the pressure of the medicament as it enters the target tissue, facilitate a change in the degree of spread of the medicament, and allow for a smooth surface as the cannula is inserted to the target tissue.

Further embodiments may comprise a cannula or stylet with multiple ports arranged in any orientation about the shaft. In an embodiment, a stylet may comprise, in application, a side port across a cannula and a side port across the stylet. In various embodiments, the side ports may be positioned such that reasonable alignment of the side ports occurs at a desired position of the stylet within the cannula such that a medicament may pass from across the reasonably aligned side ports.

Various embodiments may include a wire or other means of conveying stimulation to a target tissue. In an embodiment, the wire may extend along the cannula from about the proximal end to about the distal end of the distal tip. In another embodiment, the wire may be integral (attached to) with the cannula. In another embodiment, the wire may extend along the outside of the cannula. In another embodiment, a wire may extend along, through, or is integral with the stylet.

Design consideration that may be implemented with various embodiments include, but are not limited, to designing the wire and connector such that they may be utilized as a "plug and use" type of arrangement. A plug and use arrangement is beneficial because it reduces the complexity of the device and reduces loose wires. In an embodiment, the wire may be formed into the connector such that when the connector is connected to another medical instrument, the wire is able to communicate with the instrument. However, any connection common in the art that would allow the wire to communicate with a medical instrument may be contemplated within various embodiments.

Various embodiments may include insulation or at least one form of insulation about the cannula, stylet, or wire. As may be appreciated by one of ordinary skill in the art, any material of construction that provides electrical or thermal insulation could be used such as, but not limited to, a plastic, a rubber, a metal, a non-metal, or the like. In some embodiments, the insulation covers the exterior of the hollow cannula along the entire first length. In some embodiments, the insulation covers the exterior of the hollow cannula until it reaches the rigid bend portion of the hollow cannula. In some embodiments, the insulation covers an exterior portion of the hollow cannula in between the hub and the rigid bend portion.

Various embodiments may include insulation around the hollow cannula, flexible stylet, or wire that is constructed of a material that permits differentiation between the insulation and the hollow cannula or flexible stylet material during real-time procedural use. Numerous procedures, such as, but not limited to, fluoroscopic guidance procedures, NMR procedures, X-ray procedures, direct viewing procedures, or the like, may be used during a medical procedure to determine the position of a retrofitted neural injection system and the target location. In such embodiments, a practitioner may choose an embodiment with an insulation coating, wherein the absorptive or reflective difference between the insulation coating and the uninsulated portion of the retrofitted neural injection system can be differentiated in real-time using the selected real-time viewing system. For example, a particular insulation may absorb the energy from a real-time viewing system and show up as a dark segment whereas the uninsulated portion may reflect the energy and appear to be a bright segment. In such embodiments, the differentiation in reflectivity and absorption may provide a method to determine the exact position of the shaped tip, the distal tip, or the side portal of the retrofitted neural needle in relation to the treatment site, given the relative distance from the insulation/non-insulation border.

Further modifications of embodiments of a retrofitted injection system with a wire comprise the introduction of a probe about the shaft or wire. Various probes capable of use with embodiments include temperature probes, stimulation probes, cameras, or the like.

Various embodiments may include methods of manufacture of a retrofitted neural injection system. Various embodiments may include acquiring an injection needle comprising a hollow cannula with an open distal end. In some embodiments, the open distal end is shaped in a beveled form. Then, a side port is formed in the hollow cannula proximate to the distal end so as to permit fluid communication between the inside and the outside of the hollow cannula via the newly formed side port. In some embodiments, a plurality of side ports is formed. Formation of a side port in the hollow cannula of the injection needle may be performed using any number of methods known to ones of ordinary skill in the art. Then, the open distal end of the hollow cannula is sealed with a biocompatible sealant so as to eliminate fluid communication between the inside and the outside of the hollow cannula via the distal end. In some embodiments, the biocompatible sealant may be comprised of a thermosetting material. In some embodiments, the biocompatible sealant may be comprised of a cured epoxy resin. In some embodiments, the biocompatible sealant may be comprised of an aliphatic polymer. In some embodiments, the biocompatible sealant may be comprised of a polyfluorocarbon. Handling, applying, and curing the sealant may be performed using any number of techniques known to one skilled in the art. In some embodiments, the sealant does not hinder the penetrating or leading operation of the distal end of the hollow cannula. Then, in some embodiments, the hollow cannula is forcibly bent so as to impart a rigid bend. Then, in some embodiments, a stylet is included. Then, in some embodiments, a wire is included. Then, in some embodiments, insulation is included.

Various embodiments may include methods of use of a retrofitted injection system. An embodiment of a method may include locating a site for treatment in a patient. Then, inserting into a patient at least a portion of a retrofitted injection system comprised of an at least partially hollow cannula being defined by a first inside diameter, a first outside diameter, a first length, a side port located coaxially along the hollow cannula for fluid communication between the inside and the outside of the hollow cannula, and a sealed distal end. In some embodiments, a stylet is included, wherein the stylet is capable of being releasably locked in a first position within the hollow cannula and extends up to a first length of the hollow cannula. In some embodiments, the hollow cannula proximate to the distal end includes a rigid bend so as to facilitate placement of the distal end about the treatment site. Then, the distal end of the retrofitted neural injection system is maneuvered inside a patient proximate to the treatment site. Then, the patient is treated.

Further embodiments of a method may include stimulating a tissue. Further embodiments of a method may include ablating at least a portion of the tissue about a site. Other embodiments comprise probing a tissue. And yet further embodiments of a method may include preparing a patient for administering a medicament.

In an embodiment of an administration of a block, such as a nerve block, the method may comprise preparing the patient. In an embodiment, preparing the patient may comprise placing a patient in a supine position or extended position, without a pillow, with the patient's head in a neutral position.

In an embodiment of administration of a medicament, while standing on a side of the body that is to be blocked, a physician may tactilely locate the cricoid cartilage. In such an embodiment, the neural injection system may be inserted in a position approximately one finger breadth below the cricoid cartilage, between the carotid sheath and the trachea on the side to be blocked, while aiming slightly medially until bony contact is made with the ventral lateral side of the body of the seventh cervical vertebra. When the neural injection system is in that position, the anesthesia may be injected.

In another embodiment, there may be methods for injecting a medicament into tissue of a subject. The method may include inserting the distal portion of an embodiment into the tissue of the subject and causing a therapeutic amount of medicament to enter multidirectionally from a distal end into the tissue.

FIG. 1 illustrates an embodiment of a traditional injection system 1. The traditional injection system 1 is comprised of a cannula 10. The cannula 10 is capable of being characterized as having a first length as measured from the proximal end of a stylet mating hub 44 to a distal opening 46 of the distal tip 40. The distal tip 40 in this example is in a beveled shape at the end of a hollow cannula shaft 34. A stylet mating hub 44, wherein a stylet 20 may be insertedly attached to the cannula 10, is present on the proximal end of the cannula 10. The stylet mating hub 44 possesses a stylet receiving notch 60 to fixedly engage a corresponding tab 58 on a stylet 20.

FIG. 2 is an illustration of an embodiment of a retrofitted neural injection system 2. The retrofitted injection system 2 is comprised of similar components as the traditional injection system 1. Retrofitted neural injection system 2 is also comprised of a side port 48, which in FIG. 2 is embodied as a small rounded hole. Retrofitted neural injection system 2 is also comprised of a distal opening 46 that is sealed closed. This permits fluid communication between the inside and the outside of the hollow cannula shaft 34 only by the side port 48 instead of by the distal opening 46 as in the traditional injection system 1.

FIG. 3 is an illustration of an embodiment of a retrofitted neural injection system 3 with a rigid bend in the cannula. The retrofitted injection system 3 is comprised of similar components as the traditional injection system 1 and retrofitted neural injection system 2. Retrofitted neural injection system 3 is also comprised of rigid bent portion 38 proximate to the side port 48, which in FIG. 3 is embodied in a quadrangle hole. Retrofitted neural injection system 3 is also comprised of insulation 36 along part of the hollow cannula shaft 34.

As such, various embodiments of the present invention generally comprise methods of retrofitting a needle comprising acquiring an injection needle comprising a hollow cannula with an open distal end; forming at least one side port in the hollow cannula proximate to the distal end so as to permit fluid communication between the inside and the outside of the hollow cannula via the side port; and sealing the open distal end of the hollow cannula with a sealant so as to eliminate fluid communication between the inside and the outside of the hollow cannula via the distal end.

Various further embodiments therefore comprise a retrofitted neural injection system comprising an at least partially hollow cannula with a sharp distal end, wherein the distal end has a port, and the partially hollow cannula is defined by a first inside diameter, a first outside diameter, a first length, and at least one side port in fluid communication between the inside and the outside of the hollow cannula, located coaxially at a predetermined distance from the distal end, wherein the port at the distal end is sealed to eliminate fluid communication between the inside and the outside of the hollow cannula via the distal end.

Various further embodiments comprise a method of treatment for an individual in need thereof comprising locating a site for treatment in the individual; adjusting the retrofitted neural injection system as described herein; such that the system is positioned relative to the individual at a desired insertion point and orientation; inserting at the site at least a portion of the retrofitted neural injection system; maneuvering the distal end of the retrofitted neural injection system inside the individual proximate to the site; and treating the individual.

Although the present invention is described with several embodiments, various changes and modifications may be suggested to one skilled in the art. In particular, the present invention is described with reference to certain polymers and materials and methods of processing those materials, but may apply to other types of processing or materials with little alteration and similar results. Furthermore, the present invention contemplates several process steps that may be performed in the sequence described or in an alternative sequence without departing from the scope and the spirit of the present invention. The present invention is intended to encompass such changes and modifications as they fall within the scope and the spirit of the appended claims.

What is claimed is:

1. A method of retrofitting a needle comprising:
   acquiring an injection needle comprising a hollow cannula with an open distal end, the hollow cannula being devoid of other structure within the hollow cannula, the open distal end exhibiting a bevel having a distalmost sharp end and a proximal heel end;
   forming only one single side port in a sidewall of the hollow cannula proximate to the distal end so as to permit fluid communication between an inside and an outside of the hollow cannula via the one single side port, the remainder of the sidewall of the hollow cannula comprising an imperforate structure;
   positioning the one single side port on a side of the needle that is radially aligned with the proximal heel end to enable a user to directionally inject a fluid therapy from only the one single side port;
   disposing a mass of sealant within the hollow cannula while the hollow cannula is devoid of other structure to entirely eliminate fluid from exiting the hollow cannula via the distal end while still enabling fluid communication between the inside and the outside of the hollow cannula via the one single side port;
   positioning the mass of sealant such that the mass of sealant does not hinder penetrating or leading operations of the distal end of the hollow cannula while not encumbering or blocking the one single side port;
   solidifying the mass of sealant within the hollow cannula to form a solid mass of sealant; and
   configuring the retrofitted needle with the mass of sealant disposed in the hollow cannula to ablate target tissue in a subject.

2. The method of claim 1, wherein disposing the mass of sealant within the hollow cannula comprises plugging a beveled open distal end hollow cannula.

3. The method of claim 1, further comprising selecting the mass of sealant to comprise a biocompatible material.

4. The method of claim 3, further comprising selecting the biocompatible material to comprise a thermosetting polymer.

5. A retrofitted needle produced by the method of claim 1.

6. The method of claim 3, further comprising selecting the biocompatible material to comprise at least one of an aliphatic polymer or a polyfluorocarbon.

7. The method of claim 1, further comprising forcibly bending the hollow cannula to impart a rigid bend proximate to the sealed distal end and the one single side port.

8. The method of claim 1, wherein configuring the retrofitted needle to ablate target tissue comprises:
   coupling a wire through the retrofitted needle to a stimulation probe; and
   insulating a portion of the hollow cannula of the retrofitted injection needle to electrically insulate the portion of the hollow cannula.

9. A method of forming a needle comprising:
   defining one single side port in an at least partially hollow cannula of an injection needle to enable fluid communication between an inside and an outside of the at least partially hollow cannula through the one single side port;
   aligning the one single side port about a diameter of the at least partially hollow cannula with a heel of a beveled tip of the at least partially hollow cannula; and
   disposing a mass of sealant in the at least partially hollow cannula between the one single side port and an open distal end to block fluid communication between the one single side port and the open distal end while still enabling fluid communication between the inside and the outside of the at least partially hollow cannula via the one single side port.

10. The method of claim 9, wherein disposing the mass of sealant comprises placing a flowable mass of sealant into the at least partially hollow cannula.

11. The method of claim 9, further comprising selecting the mass of sealant to comprise a flexible material.

12. A retrofitted needle as produced by the method of claim 9.

13. The method of claim 9, further comprising:
   coupling a wire extending through the retrofitted needle to a stimulation probe;
   insulating a portion of the at least partially hollow cannula of the retrofitted injection needle to electrically insulate the portion of the at least partially hollow cannula; and
   configuring the retrofitted needle to ablate target tissue.

14. The method of claim 9, further comprising shaping the mass of sealant to entirely block fluid from traveling from the open distal end to the one single side port.

15. A method of forming a needle comprising:
   defining one single side port in an at least partially hollow cannula of an injection needle to enable fluid communication between an inside and an outside of the at least partially hollow cannula through the one single side port;
   disposing a flowable mass of material in the at least partially hollow cannula between the one single side port and an open distal end to at least partially prohibit fluid communication between the one single side port and the open distal end;
   at least partially solidifying the flowable mass of sealant.

16. The method of claim 15, further comprising shaping the flowable mass of material to entirely block fluid communication between the one single side port and the open distal end while still enabling fluid communication between the inside and the outside of the at least partially hollow cannula via the one single side port.

17. The method of claim 15, further comprising shaping the flowable mass of material to entirely block fluid from traveling from the open distal end to the one single side port while still enabling fluid communication between the inside and the outside of the at least partially hollow cannula via the one single side port.

18. The method of claim 15, further comprising shaping the mass of material to entirely fill the open distal end in a radial direction.

19. The method of claim 15, further comprising shaping the mass of material to entirely occlude fluid from flowing into the at least partially hollow cannula through the open distal end.

20. A retrofitted needle formed by the method of claim 15.

* * * * *

UNITED STATES PATENT AND TRADEMARK OFFICE
CERTIFICATE OF CORRECTION

PATENT NO. : 10,052,453 B2
APPLICATION NO. : 14/188110
DATED : August 21, 2018
INVENTOR(S) : Nicholas Sandor Racz It is certified that error appears in the above-identified patent and that said Letters Patent is hereby corrected as shown below:

In the Claims

| | | | |
|---|---|---|---|
| Claim 8, | Column 12, | Line 6, | change "a wire through" to --a wire extending through-- |
| Claim 12, | Column 12, | Line 32, | change "needle as produced" to --needle produced-- |

Signed and Sealed this
Second Day of October, 2018

Andrei Iancu
*Director of the United States Patent and Trademark Office*